United States Patent [19]

McAtee

[11] Patent Number: 5,403,350
[45] Date of Patent: Apr. 4, 1995

[54] KNEE SUPPORT AND ANGULAR ADJUSTMENT APPARATUS

[76] Inventor: Richard M. McAtee, 2245 Bermuda Dunes Pl., Oxnard, Calif. 93030

[21] Appl. No.: 134,084

[22] Filed: Oct. 8, 1993

[51] Int. Cl.[6] .............................................. A61F 5/00
[52] U.S. Cl. .................................... 606/241; 606/244; 5/648
[58] Field of Search .............. 606/241, 242, 243, 249, 606/245; 5/601, 624, 612, 648, 649, 650, 651; 297/423.45, 423.46; 248/456

[56] References Cited

U.S. PATENT DOCUMENTS

| | | | |
|---|---|---|---|
| 309,678 | 12/1884 | Aubin | 606/241 |
| 1,046,736 | 10/1912 | Clayton | 606/244 |
| 1,088,476 | 2/1914 | Stiles | 606/244 |
| 1,228,953 | 6/1917 | Naysmith | 606/244 |
| 1,390,938 | 9/1921 | Thompson | 248/456 |
| 2,346,722 | 4/1944 | Bowman | 5/648 |
| 2,465,781 | 3/1949 | Banta | 5/651 X |
| 2,732,269 | 1/1956 | Astroff | 5/648 X |
| 3,528,413 | 9/1970 | Aydt | 5/650 X |
| 4,608,969 | 9/1986 | Hamlin | 606/241 X |
| 4,700,373 | 10/1987 | Miller | 5/648 X |

*Primary Examiner*—Peter A. Aschenbrenner
*Attorney, Agent, or Firm*—Poms, Smith, Lande & Rose

[57] ABSTRACT

A device for studying patello femoral articulation in a magnetic resonance machine has an armature with a step-cut slot. The armature is pivoted to a base frame. A leg lever has two ends, a first end with a padded cross-member for accommodating lower legs or ankles, and a second end that is pivotally mounted to the base frame. The leg lever is interconnected with the step-cut slot, so that the leg lever may be positioned in vertical increments within the slot. A secondary lever is pivotally mounted to the base frame at the same location as the leg lever, and is also fixedly attached to an end portion of the leg lever. The leg lever can be incrementally raised and lowered within the step-cut slot. Furthermore, the first end of the leg lever is biased upward. The apparatus may be substantially metal-free so that the device will not distort the magnetic field inside the magnetic resonance machine.

17 Claims, 3 Drawing Sheets

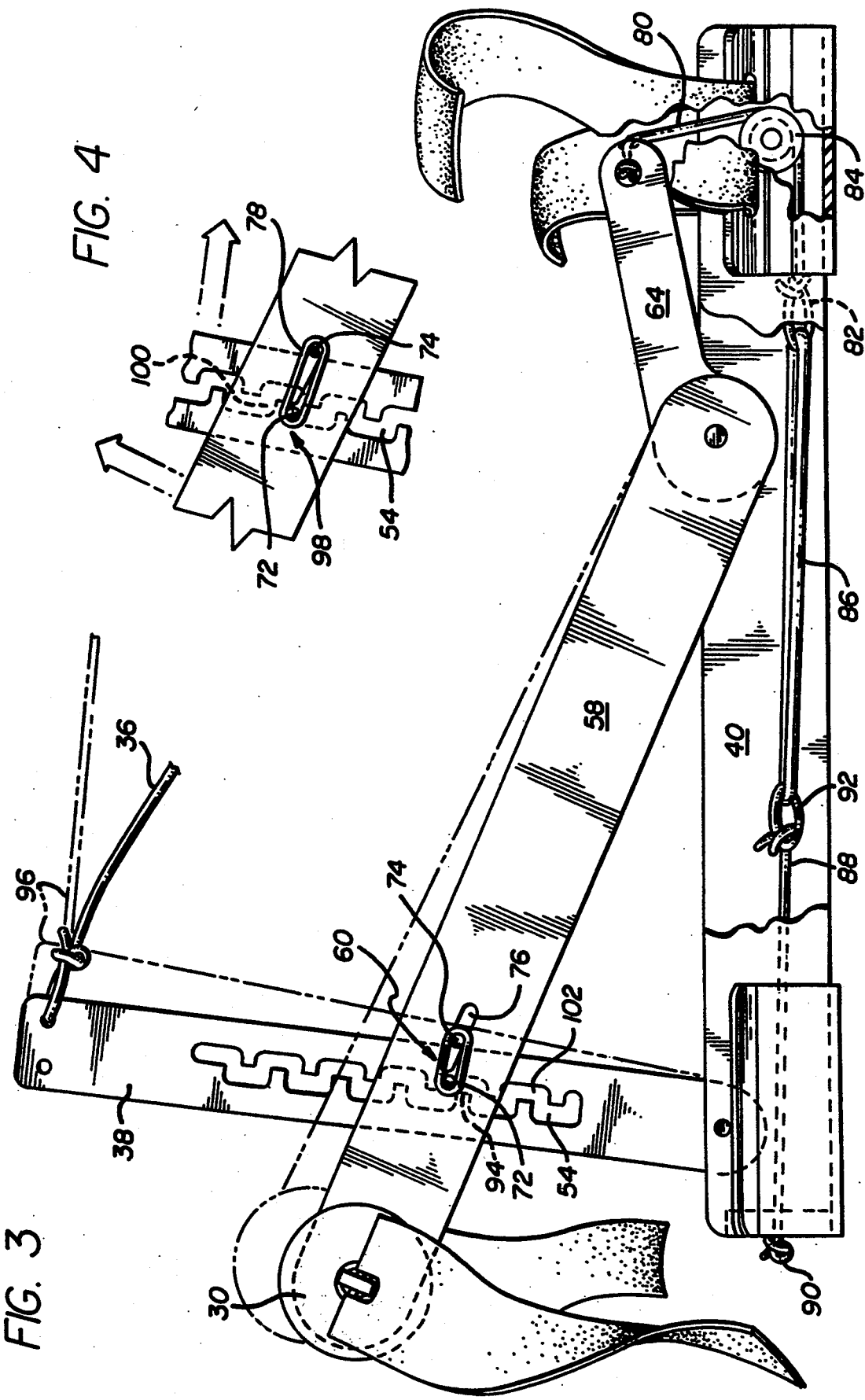

KNEE SUPPORT AND ANGULAR ADJUSTMENT APPARATUS

FIELD OF THE INVENTION

The present invention relates to an apparatus for adjusting the angular position of the knee to permit a magnetic resonance imaging machine to take a series of internal images of the knee.

BACKGROUND OF THE INVENTION

Magnetic resonance imaging (MRI) scanners offer a noninvasive and highly accurate method for assessing many types of knee injuries. Most MRI scanners are large units consisting of a long, narrow tunnel and a patient tray. The patient lies on the tray while a technician positions the patient's knee. Once the knee position is set, the technician slides the patient tray into the tunnel. The unit then exposes the patient to a strong magnetic field while taking a series of high-quality images of the knee. Ideally, the knee images are taken in specific angular increments. A physician can then get a good idea of how the knee functions as it moves through a range of motion.

Despite the great promise of MRI in the diagnosis of knee injuries, certain practical problems have arisen in properly positioning the knee for a scan. To study the relationship of the patella or knee cap, the femur or upper leg bone, and the tibia and fibula, or lower leg bones, it is desirable to obtain views of the knee with the upper and lower leg at various angular orientations. Unfortunately, when a patient lies in a prone position, gravity tends to straighten the knee. Also, an unsupported knee tends to move around over time, thereby distorting the MRI images.

Attempts to maintain the knee in a bent position within the MRI scanner have been awkward. One common approach has been to simply prop-up the knee with pillows. This approach has several major problems. First, the knee tends to change position when the pillows shift. As noted above, shifting knee position distorts the MRI images. And second, the pillow approach does not offer any means to calibrate the precise angle of the knee. Thus, a physician cannot know what angular knee position a certain image corresponds to, thereby detracting from the physician's ability to make a proper diagnosis. Further, when the angle of the knee is to be changed, the patient must be slid out of the MRI chamber, re-oriented and then slid back into the MRI apparatus, with the procedure taking much longer than would be desired, with corresponding annoyance by the patient and prolonged use of the expensive MRI apparatus.

Another approach is to employ an awkward boardlike apparatus that runs the length of the patient's body. The patient lies down prone on the board, which sits atop the patient tray. The board is hinged at about the point of the patient's knee, and the entire portion of the board distal to the patient's knees rotates to incline upward. A long lever is sometimes provided to raise or lower the hinged portion of the board.

Like the pillow approach, the board apparatus has a number of drawbacks. The apparatus does not provide set vertical positions, so exact calibration of knee angle is not practical. Storage of the apparatus is also a problem. Since the apparatus is so large, it must be removed from the MRI room when not in use. Additionally, the apparatus is clumsy and inconvenient to use.

SUMMARY OF THE INVENTION

It is desirable to provide a convenient apparatus for studying patello femoral articulation in a magnetic resonance imaging scanner. The apparatus should be easy to use and convenient to store. It should position the lower leg at fixed, incremental vertical distances so that the knee angle of rotation can be accurately determined. Additionally, the device should be substantially free of metal so as not to interfere with the magnetic field of the MRI scanner.

An apparatus that accomplishes these goals may have a base frame and an armature that is pivotally connected to the base frame. A leg lever is interconnected with the armature. The leg lever has a first end that can accommodate the lower legs or ankles, and a second end that is pivotally mounted to the base frame. The apparatus permits a user to raise and lower the leg lever in predetermined vertical increments, thereby controlling the angle of knee rotation.

In accordance with another aspect of the present invention, an apparatus for studying knee articulation of a patient for use in an MRI scanner or the like may have a base with an armature mounted to the base. A leg lever is adjustably coupled to the armature, and is pivotally mounted to the base adjacent to the patient's knees. The leg lever is provided with means to support the patient's ankles or feet. The apparatus allows the user or an attendant to remotely and progressively move the leg lever up and down relative to the armature, so that MRI scans may be taken of the patient's knee with various known relative angular orientations of the upper and lower legs.

In accordance with another more specific aspect of the present invention, a device for studying patello femoral articulation in a magnetic resonance machine may have an armature with a step-cut slot. The armature is pivoted to a base frame. A leg lever may have two ends, a first end with a padded cross-member for accommodating lower legs or ankles, and a second end that is pivotally mounted to the base frame. The leg lever may be interconnected with the step-cut slot, so that the leg lever may be positioned in vertical increments within the slot.

In accordance with a biasing feature of the present invention, a secondary lever may be pivotally mounted to the base frame at the same location as the leg lever, at about the level of the patient's knee joint. The secondary lever may also be fixedly attached to the end portion of the leg lever. A biasing system may be connected to the secondary lever such that the padded cross-member is biased upwardly. This biasing means may include a resilient member that pulls down on the secondary lever to rotate the leg lever upwardly.

As another feature, the leg lever may have two spaced structural members with the armature being positioned in between the two spaced members. Each of the two spaced members may have an aperture and an elongated slot. A first peg may pass through each aperture and through the step-cut slot of the armature. A second peg would pass through each elongated slot on an outer edge of the armature. A resilient band may interconnect the first peg and the second peg, thereby biasing the pegs toward one another.

As an additional feature, the present invention may be substantially metal-free so that the device will not distort the magnetic field inside the magnetic resonance machine.

Other objects, features, and advantages of the present invention will become apparent from a consideration of the following detailed description and from the accompanying drawings.

BRIEF DESCRIPTION OF THE DRAWINGS

FIG. 3 is a side view of the apparatus of FIG. 3 showing the relative motion of the leg lever and the armature as the armature travels downward;

FIG. 4 is a detailed view of the step-cut slot and interconnecting mechanism of the apparatus of FIG. 2 showing that the position of the two pegs changes relative to one another as the leg lever travels through the step-cut slot.

DETAILED DESCRIPTION OF THE PREFERRED EMBODIMENTS

Figure 1:
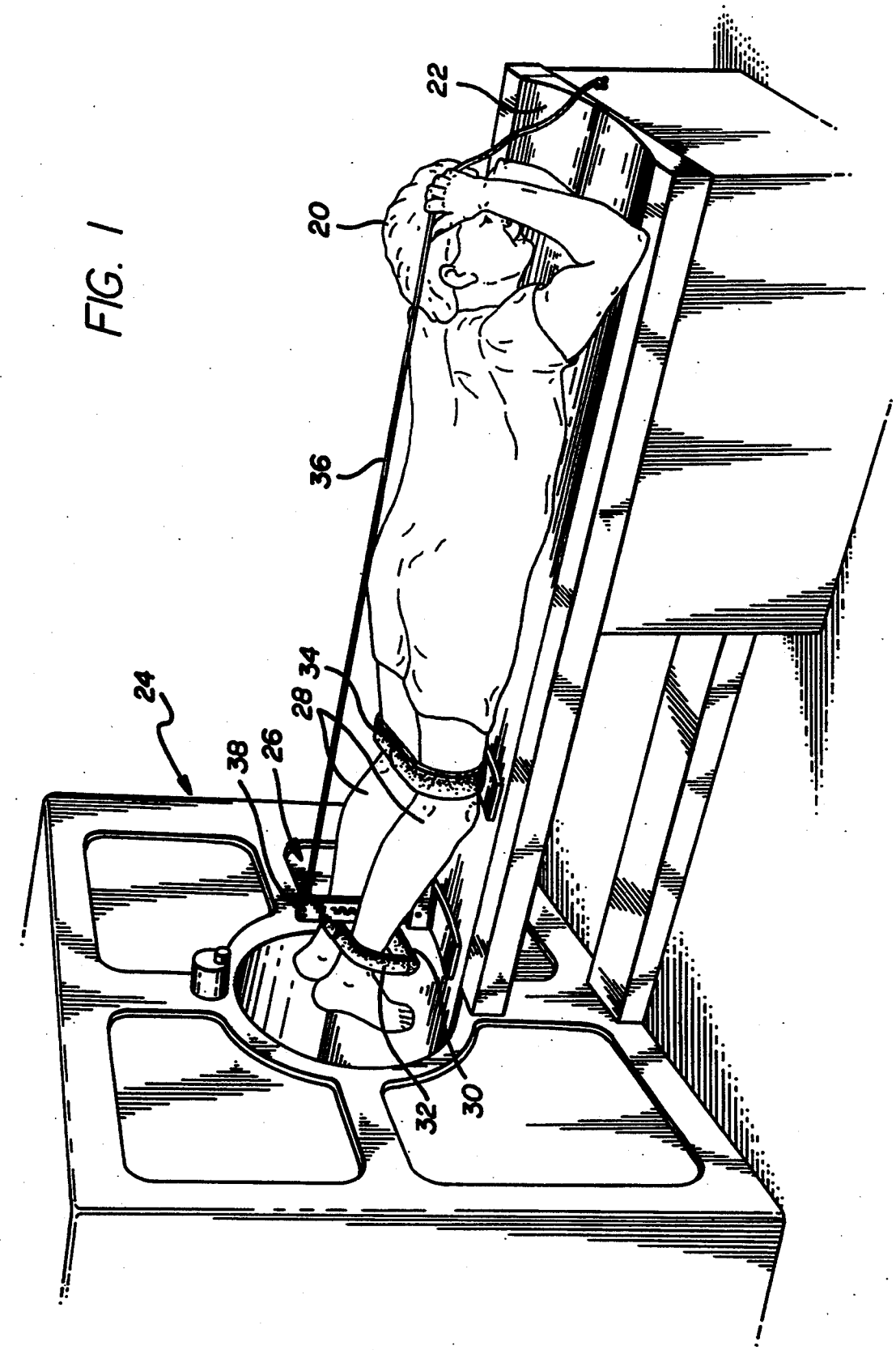
FIG. 1 is a perspective view showing a patient adjusting the angle of his lower legs prior to entering a magnetic resonance imaging scanner.

Referring more particularly to the drawings, FIG. 1 shows a patient 20 lying in a prone position on a patient tray 22 of a magnetic resonance imaging machine 24. Knee positioning apparatus 26 holds the patient's ankles or lower legs 28 against padded cross-bar 30 with ankle strap 32. Mid-leg strap 34 secures the middle portion of the patient's legs just above the knee to the apparatus 26.

FIG. 1 shows that the patient 20 is grasping control cord 36, which is attached to armature 38 of the apparatus. When the patient pulls the cord, the weight of the patient's lower legs 28 push cross-bar 30 down one notch. Alternately, when the patient removes the weight of his legs from off of the cross-bar simultaneously with pulling the cord, the cross-bar will ascend one notch. After the patient has placed his legs in the desired position, a technician slides patient tray 22 into the MRI scanner where the knee images are taken.

Figure 2:
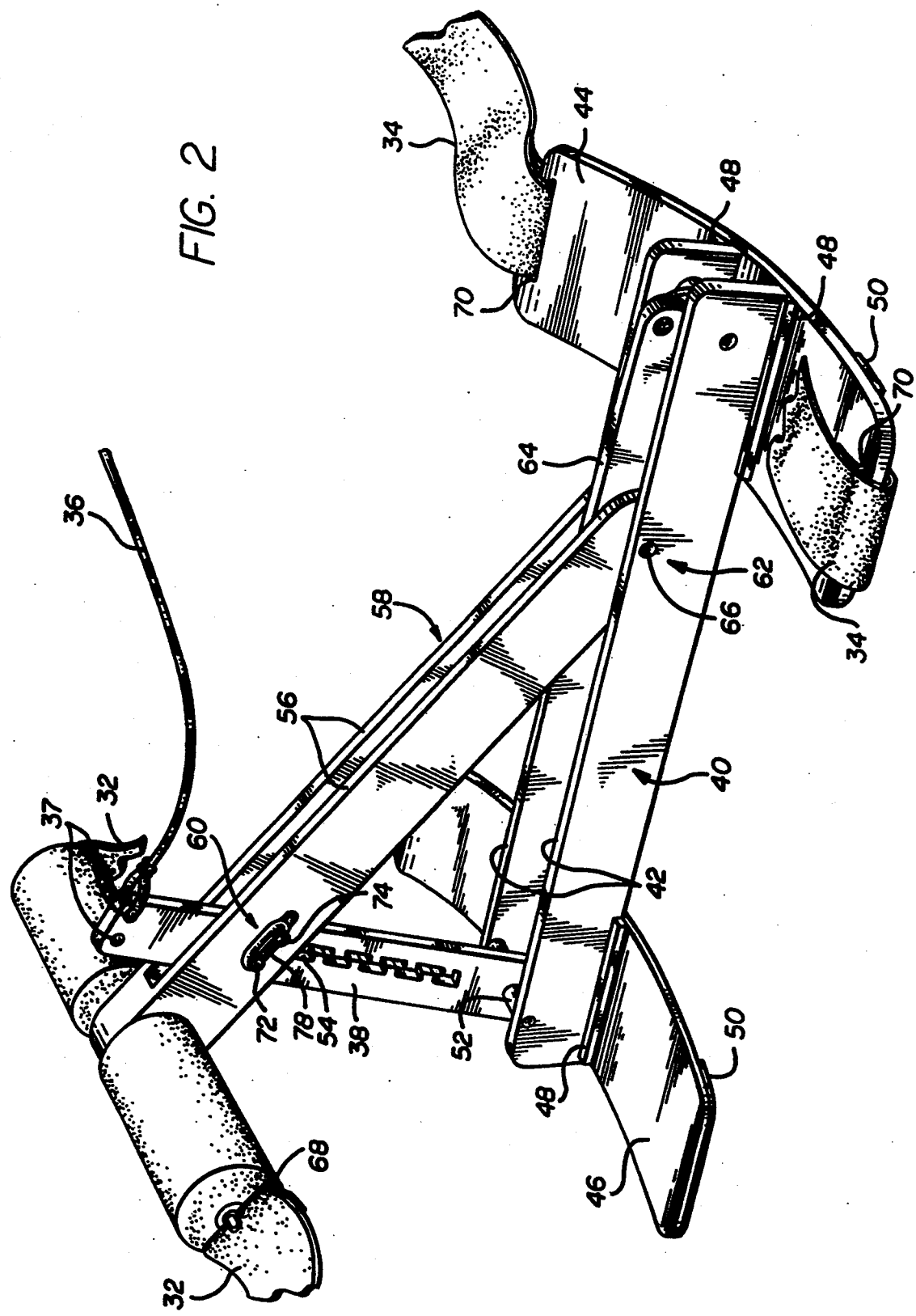
FIG. 2 is a perspective view of one embodiment of the present invention.

FIG. 2 shows a preferred embodiment of the knee positioning apparatus in some detail, but with some parts removed, for clarity. The apparatus has a base frame 40 with two spaced beams 42. A forward base cross piece 44 and a rear base cross piece 46 are attached to the forward and rear portions of base frame 40, respectively. Structural braces 48 prevent beams 42 from moving relative to the cross pieces. Cross-pieces 44 and 46 are provided with pads 50 for cushioning, and to reduce wear against patient tray 22.

Armature 38 is mounted on pivot pin 52, which fits through apertures provided in beams 42. The armature includes a lengthy step-cut slot 54 and control cord apertures 37 through which control cord 36 may be fastened. Armature 38 passes through the two leg lever beams 56 of leg lever 58. Resilient stop mechanism 60 interconnects leg lever 58 with the step-cut slot 54 of armature 38.

Leg lever 58 is pivotally attached to base frame 40 at fulcrum 62. As shown in FIG. 3, secondary lever 64 is fixedly attached to the two leg lever beams 56 and is pivotally attached to base frame 40 at fulcrum 62. Secondary lever 64 and leg lever 58 both pivot about a common pivot pin 66, which is supported by apertures in beams 42 of base frame 40. Fulcrum 62 is located at about the level of the patient's knee joint.

Two lower leg strap segments 32 attach to the sides of padded cross member 30. Each strap segment may be folded over and sewn at the end to form a loop 68. The loop 68 may then pass through a peg (not shown) inserted through an eyelet integral with cross piece 30. Two mid-leg strap segments 34 attach directly to forward base cross piece 44 at apertures 70. Individual strap segments 32 and 34 may have a VELCRO backing to adjust to the size of a patient's legs.

FIG. 3 shows additional features of a preferred embodiment of the present invention. Resilient stop mechanism 60 has an inner post 72 that travels within step-cut slot 54. Inner post 72 fits snugly into apertures cut through both leg lever beams 56, so that inner post 72 is secured to leg lever 58. Outer post 74 travels within leg lever slots 76 and along the edge of armature 38. FIG. 2 illustrates that a resilient member 78 interconnects inner post 72 and outer post 74, thereby biasing the posts together, and biasing armature 38 in the counterclockwise direction and to the left, as shown in FIGS. 2 and 3. Resilient member 78 may be made of any resilient material, such as rubber bands.

As best shown in FIG. 3, secondary lever 64 is connected to a system for biasing leg lever 58 upward. The system consists of a first biasing cord 80 that is affixed on one end to the secondary lever 64 and has a loop 82 on the other end. The cord 80 passes around a pulley 84 and is connected to a resilient member 86, which may be several rubber bands or other resilient material. An anchoring cord 88 passes through an opening in the base frame 40 where it is secured with a knot 90. A loop 92 on the other end of anchoring cord 88 interconnects with resilient band 86. As the leg lever rotates counterclockwise, secondary lever 64 rotates upward, thereby putting the resilient member 78 into tension. The biasing cord 80 then pulls down on the end of the secondary lever, causing the leg lever to be biased upward in a clockwise direction, as levers 64 and 58 are rigidly secured together, as mentioned above.

In the absence of weight on padded cross-member 30, inner post 72 will abut an upward stop surface such as 94 within the step-cut slot 54, and at the right hand side of the slot. To raise the padded cross-member 30 by one notch, the patient or a technician pulls on control cord 36, thereby rotating armature 38 clockwise in a forward direction into position 96, against the biasing force of rubber band 78. Inner post 72 then slides substantially horizontally across the slot until it is free of upward stop 94. FIG. 4 shows that the biasing force rotates the leg lever 58 in a clockwise direction, which would cause inner post 72 to move up to the next upward stop surface 98 on the left hand side of the slot 54. However, once the force on control cord 36 is released, since inner post 72 and outer post 74 are biased toward each other by resilient member 78, the inner post will continue to move to the right in FIG. 4 until it has slid over and up to upward stop 100. By repeatedly pulling on the control cord, the technician can cause the inner post to move incrementally to the top of the step-cut slot.

The apparatus also works in reverse. With the weight of the patient's legs resting on padded cross member 30, the patient overcomes the normal clockwise bias force on leg lever 58. Inner post 72 then tends to rest on a downward stop within and to the right hand side of the step-cut slot 54. Such a downward stop is illustrated at 102 in FIG. 3. By pulling the control cord 36, the patient causes inner post 72 to first move backward to the left across the slot, then drop down one notch to the next downward stop. This capacity to incrementally travel either downward or upward enables the patient or technician to incrementally raise or lower the ankles, causing the lower leg to rotate about the knee.

In practice, the patient may be shifted into the MRI tunnel with leg lever 58 all the way up. There, successive MRI scans may be taken rapidly with the leg lever incremented down between scans, without removing the patient from the MRI apparatus.

It should be noted that a manufacturer can alter the spacing of the steps within the step-cut slot to control the distance that the padded cross-member travels in each increment. Generally speaking, the range of rotation falls somewhere between full extension of the leg (0 degrees rotation relative to the knee) to approximately 35 degrees rotation. The upper bound of rotation is controlled by the limited space inside the tunnel of the MRI scanner. Thus, a wide tunnel will allow rotation greater than 35 degrees.

By way of example, and not of limitation, an embodiment of the present invention may have the following dimensions. Each beam 42 of base frame 40 may be 19 inches long, 2 inches high and $\frac{3}{8}$ inches thick. Armature 38 may be $11\frac{1}{2}$ inches long, $1\frac{1}{2}$ inches wide and $\frac{1}{4}$ inches thick. Step-cut slot 54 may be 6 inches long and $\frac{1}{2}$ inch wide at the widest point. Padded cross member 30 may be 11 inches wide and $2\frac{1}{4}$ inches in diameter. Each leg lever beam 56 of leg lever 58 may be 17 inches long, 2 inches high and $\frac{3}{8}$ inches thick. Secondary lever 64 may be 5 inches in length as measured from pivot pin 66 to the end of the lever, 1 inch wide along most of its length and $\frac{3}{8}$ inches thick. Cross pieces 44 and 46 may be 15 inches long, 4 inches wide, and $\frac{1}{4}$ inch thick. These sizes can all be varied to accommodate different size patients and/or the relevant dimensions of the MRI scanner and patient table.

As for materials, the present apparatus may be constructed from a wide variety of non-metallic materials, such as acrylic or wood. Of course, a number of other plastics or composite materials can be used. Structural components may be attached to one another by a variety of well known glues, such as epoxy, or mechanical fasteners such as nails, screws and so on.

In conclusion, it is to be understood that the foregoing detailed description and the accompanying drawings relate to preferred embodiments of the invention. Various changes and modifications may be made without departing from the spirit and scope of the invention. Thus, by way of example and not of limitation, the resilient members can be non-metallic springs made of a plastic, composites, or other materials, rather than rubber bands. Instead of using an additional or secondary lever, the main leg lever may be directly acted upon by the biasing arrangements. The step-cut slot 54 can be replaced with slots or notches provided on the exterior edge of the armature. Alternately, the step-cut slot may be cut with a variety of patterns other than that illustrated in the drawings.

Yet another variation involves replacing armature 38 with a threaded, rotatable rod. A matching threaded ring or shaft would be provided on leg lever 58 to mesh with the threads on the rod. A technician would rotate the rod remotely with a handle, causing the threaded ring or shaft to travel up or down along the threaded rod.

Other variations include replacing control cord 36 with a strap, or even with a rigid, lightweight member. Cross-pieces 44 and 46 can have any shape necessary to match the shape of the patient tray for providing stability. The cylindrical pads of padded cross member 30 can be replaced with contoured members having indentations to hold the ankles or lower shins.

Accordingly, the present invention is not limited to the specific embodiment shown in the drawings and described in the detailed description.

What is claimed is:

1. A device for studying patello femoral articulation in a magnetic resonance imaging scanner, the device comprising:

an armature having a step-cut slot, said armature being pivoted to a base frame;

a leg lever having two ends, a first end including a padded cross-member for accommodating lower legs or ankles, and a second end being pivotally mounted to the base frame;

interconnecting means for interconnecting said leg lever and said step-cut slot, so that said leg lever may be positioned in vertical increments within said step-cut slot;

a secondary lever that is pivotally mounted to the base frame at the same location as the leg lever, the secondary lever being fixedly attached to an end portion of the leg lever at the end of the leg lever;

biasing means connected to said secondary lever for biasing said leg lever such that said first end is biased upwardly; and means for incrementally raising and lowering said leg lever within said step-cut slot, wherein the device is substantially metal-free so that the device can be used in a magnetic resonance machine.

2. A device as defined in claim 1, wherein said armature and said leg lever are pivotally mounted to a main base portion, and said base further comprises a forward base cross piece and a rear base cross piece, said cross pieces being perpendicular to said main base portion.

3. A device as defined in claim 2, wherein said cross pieces have convex, upwardly curved profiles.

4. A device as defined in claim 1, wherein said biasing means comprises:

a cord having a first cord end that is affixed to said secondary lever, and a second cord end;

a pulley, said cord passing around said pulley; and resilient means attached to said second cord end for putting said cord in tension.

5. A device as defined in claim 1, wherein said leg lever comprises two spaced structural members, said armature being positioned in between the two spaced structural members.

6. A device as defined in claim 5, wherein each of said spaced structural members has an aperture and an elongated slot, and wherein said interconnecting means comprises:

a first peg and a second peg, said first peg passing through each aperture and through the step-cut slot, said second peg passing through each elongated slot; and resilient connecting means to resiliently connect the first peg with the second peg.

7. A device as defined in claim 2, wherein the device further comprises a strap for securing lower legs to said padded cross-member.

8. An apparatus for studying the articulation of a patient's knee for use in an MRI scanner or the like comprising:

a base;

an armature mounted to said base;

a leg lever having an upper portion and a lower portion, said leg lever being pivotally mounted at its lower portion to said base, said leg lever including on its upper portion a cross-member for supporting the ankles or feet of a patient;

said leg lever being adjustably coupled to said armature;

a control member connected to and extending from the armature for remotely and incrementally repositioning said leg lever relative to said armature; and said base including a biasing mechanism connected to said leg lever for biasing said cross-member substantially upwardly;

whereby MRI scans may be taken of a patient's knee with various relative angular orientations of the upper and lower legs without removing the patient from the MRI apparatus.

9. An apparatus as defined in claim 8, wherein said base further comprises a forward base cross piece and a rear base cross piece, said cross pieces being perpendicular to said main base portion.

10. An apparatus as defined in claim 8, wherein the device further comprises a biasing system for rotationally biasing said leg lever so that said first end is biased substantially upwardly.

11. An apparatus as defined in claim 8, wherein said leg lever comprises two spaced structural members, and said armature is positioned in between the two spaced structural members.

12. An apparatus as defined in claim 8, wherein each of said spaced structural members has an aperture and an elongated slot, and wherein said interconnecting means comprises:

a first peg and a second peg, said first peg passing through each aperture and through the step-cut slot, said second peg passing through each elongated slot; and resilient connecting means to resiliently connect the first peg with the second peg.

13. An apparatus as defined in claim 8, wherein the device further comprises a strap for securing lower legs to said device.

14. An apparatus as defined in claim 8, wherein the device can hold a patient's knee in any one of a plurality of incremental positions ranging from full extension to 35 degrees flexion.

15. An apparatus for incrementally rotating the lower leg about the knee, the device comprising:

a base frame;

an armature that is pivotally mounted to the base frame;

a leg lever that is interconnected with said armature, said leg lever having a first end including a member for accommodating lower legs or ankles and a second end that is pivotally mounted to the base frame;

said armature having an interior slot with incremental stops therein;

an interconnection post, said post interconnecting said armature and said leg lever, said post engaging with said slot; and said armature supporting said leg lever when said interconnecting post is positioned at one of said incremental stops, such that a user may incrementally raise and lower said leg lever by moving said interconnection member from one incremental stop to another;

wherein said leg lever comprises two spaced structural members, and said armature is positioned in between the two spaced structural members of the leg lever.

16. An apparatus for incrementally rotating the lower leg about the knee, the device comprising:

a base frame;

an armature which is pivotally mounted to said base frame;

a leg lever that is interconnected with said armature, said leg lever having a first end having a cross-member for accommodating lower legs or ankles and a second end that is pivotally mounted to the base frame;

said leg lever comprising two spaced structural members; and a portion of said armature being positioned in between said two spaced structural members.

17. A device as defined in claim 16, wherein:

said base frame has a first end, a second end and a transverse base support;

said armature has an upper end and a lower end, said armature being pivotally mounted at its lower end to said second end of said base;

said armature having a length, an armature slot extending along a portion of said length, and a plurality of incremental stop positions associated with said armature slot; and a post which extends from said leg lever and which extends through said armature slot, thereby interconnecting said armature with said leg lever;

wherein said armature supports said leg lever when said post is positioned at one of said incremental stop positions, and a user may disengage said post from said stop positions to vertically reposition said leg lever.

* * * * *